United States Patent [19]
Hama et al.

[11] Patent Number: 5,312,759
[45] Date of Patent: May 17, 1994

[54] METHOD FOR MEASUREMENT OF FRUCTOSAMINES USING 1,2-QUINONES

[75] Inventors: Michio Hama; Michiyo Nakayama; Mitsunao Tanaka, all of Tokyo, Japan

[73] Assignee: Iatron Laboratories, Inc., Tokyo, Japan

[21] Appl. No.: 741,432
[22] PCT Filed: Dec. 20, 1989
[86] PCT No.: PCT/JP90/01653
  § 371 Date: Aug. 2, 1991
  § 102(e) Date: Aug. 2, 1991
[87] PCT Pub. No.: WO91/09314
  PCT Pub. Date: Jun. 27, 1991

[30] Foreign Application Priority Data
  Dec. 20, 1989 [JP] Japan .................. 1-330165

[51] Int. Cl.$^5$ .............. G01N 33/48; G01N 33/66; G01N 33/68
[52] U.S. Cl. .................... 436/87; 436/88; 436/95; 436/164; 436/904
[58] Field of Search .......... 436/87, 88, 95, 164, 436/811, 904; 552/291

[56] References Cited
U.S. PATENT DOCUMENTS

| | | | |
|---|---|---|---|
| 2,981,606 | 4/1961 | Keston | 436/95 X |
| 3,418,083 | 12/1968 | Rey et al. | 436/95 X |
| 3,576,815 | 4/1971 | Doyle | 436/904 X |
| 3,791,988 | 2/1974 | Josef et al. | 436/95 X |
| 4,251,629 | 2/1981 | Yamanisi et al. | 436/95 X |
| 4,391,906 | 7/1983 | Bauer | 436/95 X |
| 4,427,770 | 1/1984 | Chen et al. | 422/56 X |
| 4,637,978 | 1/1987 | Dappan | 422/56 X |
| 4,642,295 | 2/1987 | Baker | 436/87 |
| 4,746,607 | 5/1988 | Mura et al. | 436/904 X |
| 4,879,243 | 11/1989 | Mura et al. | 436/904 X |
| 4,956,301 | 9/1990 | Ismail et al. | 436/87 |
| 5,002,893 | 3/1991 | Rosenthal | 436/87 |
| 5,013,647 | 5/1991 | Town et al. | 435/25 |
| 5,055,388 | 10/1991 | Vogt et al. | 436/904 X |
| 5,094,943 | 3/1992 | Siedel et al. | 435/25 |
| 5,110,745 | 5/1992 | Knicka et al. | 436/87 |

FOREIGN PATENT DOCUMENTS

| | | | |
|---|---|---|---|
| 0691365 | 7/1964 | Canada | 436/95 |
| 0094161 | 11/1983 | European Pat. Off. | |
| 291061 | 11/1988 | European Pat. Off. | |
| 63-180861 | 7/1988 | Japan | 436/95 |
| 2-184758 | 7/1990 | Japan | 436/88 |
| 2297065 | 12/1990 | Japan | |

OTHER PUBLICATIONS

A. Gottschalk Biochem J. 1952, 52, 455–460.
R. F. Homer et al. Nature 1959, 1984, 2012–2013.
V. H. Tiedemann et al., Z. Naturfar. 1961, 16B, 120–126.
D. N. Kramer e al., J. Org. Chem. 1967, 32, 1163–1165.
G. V. Fomin et al., Chem. Abstr. 1968, 69, 93032z.
G. V. Fomin et al., Chem. Abstr. 1969, 70, 25674f.
R. H. Dekker et al., Eur. J. Biochem. 1982, 125, 69–73.
E. D. Schleicher et al., Clin. Chem. 1988, 34, 320–323.
R. Flückiger et al. Biochem. Biophys. Res. Commun. 1988, 153, 353–358.
M. A. Paz et al. Biochem. Biophys. Res. Commun. 1988, 154, 1330–1337.
P. M. Gallop et al. Trends Biochem. Sci. 1989, 14, 343–346.
A. F. Jones et al. Clin. Chem., 1987, 31, 147–149.
P. A. Trudinger "On the Absorbancy of Reduced Methyl Viologen" Anal. Biochem., 1970, 36, 222–225.

Primary Examiner—James C. Housel
Assistant Examiner—A. Soderquist
Attorney, Agent, or Firm—Burgess, Ryan and Wayne

[57] ABSTRACT

A method for measurement of fructosamines in an aqueous liquid characterized by including the steps of:
  (a) bringing an aqueous liquid sample into contact with one or more active oxygen producing substances;
  (b) bringing the product of said step (a) into contact with a reagent producing a detectable change in the presence of hydrogen peroxide derived from the active oxygen, and
  (c) detecting an occurrence of the detectable change of said step (b).

6 Claims, 2 Drawing Sheets

Amount of glycosylated albumin
(as conversion to 5-HMF, μM)

Amount of glycosylated albumin
(as conversion to 5-HMF, μM)

METHOD FOR MEASUREMENT OF FRUCTOSAMINES USING 1,2-QUINONES

TECHNICAL FIELD

The present invention relates to a method of measurement of fructosamines in an aqueous liquid.

BACKGROUND ART

When glucose and protein react in the blood, stable fructosamines are formed through the unstable Shiff bases. The concentration of fructosamines in the blood has correlation with the concentration of glucose in the blood. Further, it is hardly affected by even short-term variations in the glucose concentration. Therefore, it is known to be extremely effective to measure the concentration of fructosamines in the blood so as to diagnose diabetes and monitor the progress of treatment of diabetics.

Japanese Examined Patent Publication (Kokoku) No. 1-13062 describes a method for measuring the concentration of fructosamines in a blood sample by using the fact that fructosamines have reducing activity under alkaline conditions and cause a color agent (for example, a tetrazolium salt) to produce color. This method is preferable in the point that it can be applied to an automatic measurement apparatus. However, blood samples contain reducing substances (for example, ascorbic acid, glutathione, and uric acid) in addition to fructosamines. Therefore, it was necessary to perform the measurement after a certain time elapses from the start of the reaction so as to reduce or avoid the effects of these nonspecific reducing substances.

Various proposals were made on techniques for eliminating the influence of coexisting substances. For example, Japanese Unexamined Patent Publication No. 63-15168 describes a method for removal of the nonspecific reducing components and turbidity inducing components by making use of a neutral pH value. Further, Japanese Unexamined Patent Publication No. 63-304999 describes a method for removing the nonspecific reducing components and turbidity inducing components by uricase or a surface active agent and performing the measurement in a single stage. Further, Japanese Unexamined Patent Publication No. 63-182567 describes a method for measuring fructosamines after performing a step for removing interfering substances in advance and Japanese Unexamined Patent Publication No. 1-108997 describes a method for removing interfering substances by an agent oxidizing enzymes, etc.

However, in the methods described in the above patent publications, a tetrazolium salt is used as the optimal coloring agent in the same way as the method described in said Japanese Unexamined Patent Publication No. 1-13062. This tetrazolium salt produces the water insoluble coloring substance, formazane, as a result of a reaction. Formazane easily adheres to equipment of a measuring apparatus and is difficult to remove. Further, the surface active substances coexisting in a liquid sample (for example, lipids and proteins) result in a change of the apparent absorbance of formazane, so the measurement results are affected by lipids and proteins and there was the problem of a reduction in the measurement precision.

The present inventors engaged in studies to resolve the above problems and as a result discovered that if a specific compound is brought into contact with fructosamines, active oxygen is produced and hydrogen peroxide is derived from that active oxygen, so by measuring the amount of the hydrogen peroxide, it is possible to measure the fructosamines. The present invention is based on this discovery.

DISCLOSURE OF INVENTION

Therefore, the present invention relates to a method for measurement of fructosamines in an aqueous liquid which comprises the steps of:
(a) bringing an aqueous liquid sample into contact with one or more active oxygen producing substances;
(b) bringing the product of said step (a) into contact with a reagent producing a detectable change in the presence of hydrogen peroxide derived from the active oxygen, and
(c) detecting an occurrence of the detectable change of said step (b).

BEST MODE FOR CARRYING OUT THE INVENTION

Figure 1:
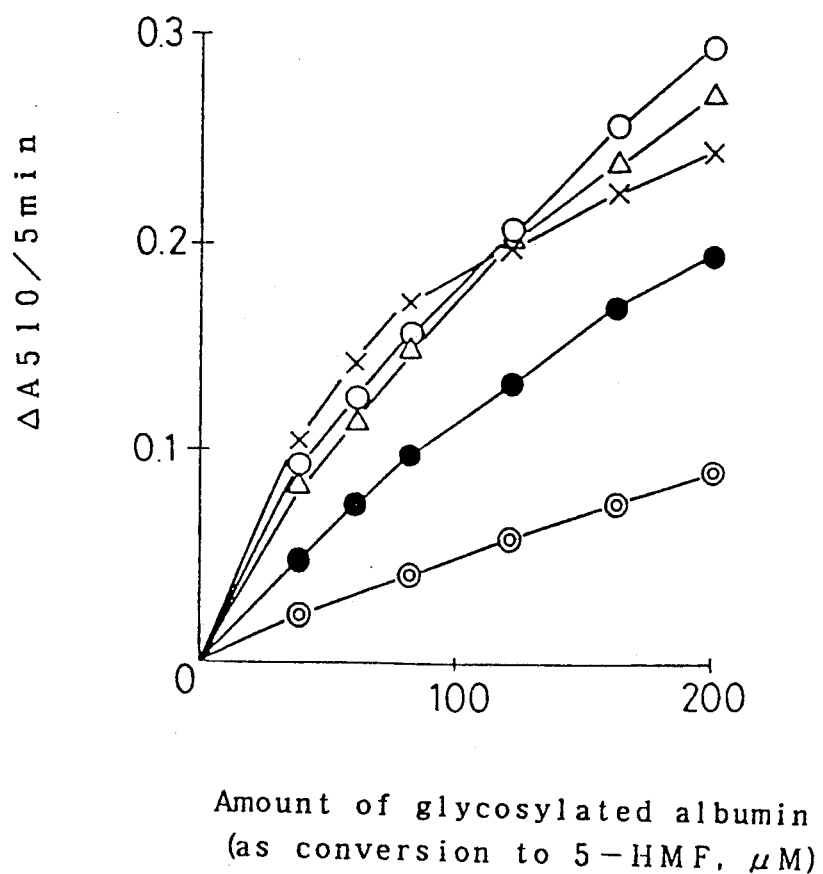
FIG. 1 is a graph showing the relationship between the amount of glycosylated albumin and the absorbance.

The "active oxygen producing substance" used in the method of the present invention means a compound which can produce active oxygen ($O_2^-$) when coming into contact with fructosamines having reducible property.

In the method of the present invention, as the active oxygen producing substance, there may be employed, for example, a phenazinium compound of the general formula:

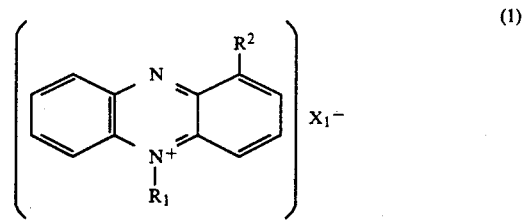

wherein, $R_1$ is a lower alkyl group having 1 to 4 carbon atoms, in particular a methyl or ethyl group, $R_2$ is a hydrogen atom, a lower alkyl group having 1 to 4 carbon atoms, in particular a methyl or ethyl group, or a lower alkoxyl group having 1 to 4 carbon atoms, in particular a methoxy group, and $X_1$ is an anion, for example, a lower alkylsulfate having 1 to 4 carbon atoms, in particular methyl or ethyl sulfate. As the phenazinium compound of the formula (1), 1-methoxy-5-methylphenazinium methylsulfate is preferably used. The phenazinium compound of the formula (1) is brought into contact with the sample in a range of pH of 8.5 to 11.0, preferably 9.5 to 10.3.

Further, in the method of the present invention, as the active oxygen producing substance, there may be used a bipyridine compound of the general formula:

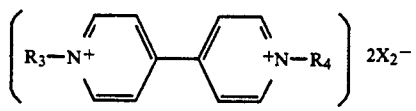
(2)

wherein $R_3$ and $R_4$ are independently lower alkyl groups having 1 to 4 carbon atoms, in particular methyl or ethyl groups, and $X_2$ is an anion, for example, a halogen, in particular chlorine or bromine. As the bipyridine compound of the formula (2), 1,1'-dimethyl-4,4'-bipyridiriumdichloride [Methyl viologen] is preferably used. The bipyridine compound of the formula (2) is brought into contact with the sample at a range of pH of 8.5 to 11.0, preferably 9.5 to 10.3.

Further, in the method of the present invention, as the active oxygen producing substance, there may be employed a 1,4-quinone compound of the general formula:

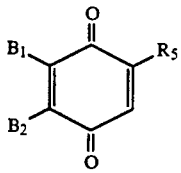
(3)

wherein, $R_5$ is a hydrogen atom or a lower alkyl group having 1 to 4 carbon atoms, particularly a methyl or ethyl group, $B_1$ and $B_2$ are each hydrogen atoms or are atoms necessary for forming a benzene ring together with the two carbon atoms in the formula (3). As the 1,4-quinone compound of the formula (3), benzoquinone, 1,4-naphthoquinone, or 2-methyl-1,4-naphthoquinone is preferably used. The 1,4-quinone compound of the formula (3) is brought into contact with the sample in a range of pH of 8.5 to 11.0, preferably 9.5 to 10.5.

Further, in the method of the present invention, as the active oxygen producing substance, there may be used a 1,2-quinone compound of the general formula:

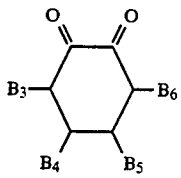
(4)

wherein, $B_3$ and $B_4$ are respectively hydrogen atoms or are atoms necessary for forming a benzene ring or a substituted or unsubstituted pyridine ring together with the two carbon atoms in the formula, and $B_5$ and $B_6$ are atoms necessary for forming a benzene ring or a substituted or unsubstituted pyrrole ring together with the two carbon atoms in the formula. The substituent optionally present on the pyridine ring or pyrrole ring is, for example, a lower alkyl group having 1 to 4 carbon atoms or carboxyl group. As the 1,2-quinone compound of the formula (4), 1,2-naphthoquinone, 9,10-phenanthrenequinone, or pyrroloquinoline quinone(2,7,9-tricarboxy-1H-pyrrolo[2,3-f]quinoline-4,5-dione) is preferably used. The 1,2-quinone compound of the formula (4) is brought into contact with the sample in a range of pH of 8.5 to 11.0, preferably 9.5 to 10.5.

Further, in the method of the present invention, as the active oxygen producing substance, there may be employed a tetrazolium salt of the general formula:

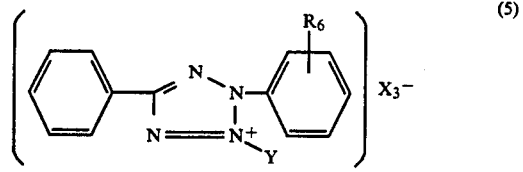
(5)

wherein, Y is a halogenated phenyl group (in particular a iodophenyl group), a substituted or unsubstituted thiazolyl group (for example, a thiazolyl group monosubstituted or disubstituted with a lower alkyl group having 1 to 4 carbon atoms, in particular, a methyl or ethyl group), or a group of

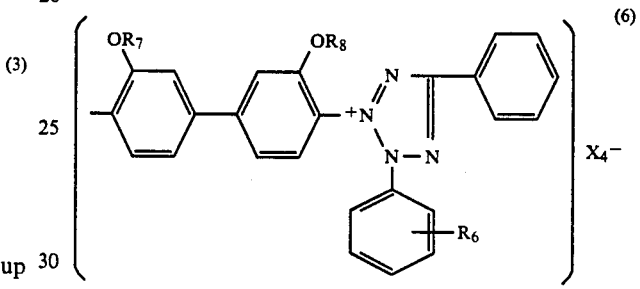
(6)

where $R_6$ is a hydrogen atom or nitro group, $R_7$ and $R_8$ are independently lower alkyl groups having 1 to 4 carbon atoms, in particular methyl or ethyl groups, and $X_3$ and $X_4$ are independently anions, for example, halogens, in particular chlorines or bromines. As the tetrazolium salt of the formula (5), 3-(p-iodophenyl)-2-(p-nitrophenyl)-5-phenyl-2H tetrazolium chloride [INT], 3-(4,5-dimethyl-2-thiazolyl)-2,5-diphenyl-2H tetrazolium bromide [MTT], or 3,3'-(3,3'-dimethoxy-4,4'-biphenylylene)-bis[2-(p-nitrophenyl)-5-phenyl-2H tetrazolium chloride] [Nitro-TB] is preferably used. The tetrazolium salt of the formula (5) is brought into contact with the sample in a range of pH of 8.5 to 11.0, preferably 9.5 to 10.5.

In the method of the present invention, measurement is made of the fructosamines contained in an aqueous liquid, in particular a biological aqueous liquid, for example, blood or liquids derived from blood (in particular, serum or plasma) or urine or tissue extracts.

In the method of the present invention, it is preferable to remove the interfering substances optionally present in the sample, before bringing the sample into contact with the active oxygen producing substance. The interfering substances are, for example, reducing substances other than fructosamines (for example, ascorbic acid, glutathione, and uric acid) and turbidity inducing components (for example, chyle). To remove the interfering substances, there may be used known methods, for example, the methods described in Japanese Unexamined Patent Publication No. 63-15168, Japanese Unexamined Patent Publication No. 63-304999, Japanese Unexamined Patent Publication No. 63-182567, or Japanese Unexamined Patent Publication No. 1-108997.

For example, the sample may be treated by dialysis or gel filtration desalination or be allowed to stand for a long period (for example, over 30 minutes) so as to remove the interfering substances. Further, it is possible to add an enzyme not affecting an ultimate results of the measurement system of the present invention. For example, it is possible to add ascorbate oxidase to remove the ascorbic acid. Further, it is possible to use a surface active agent (for example, sodium laurylsulfate) to remove the turbidity of the sample or the influence of the chyle.

The fructosamine is converted to an enol type having reducing property under alkaline conditions. In the method of the present invention, there may be used any buffers which can render the system alkaline (for example, a pH of 8.5 to 11.0, preferably a pH of 9.0 to 10.5, in particular a pH of 9.5 to 10.3). As the buffer, there may be used, for example, Good's buffer or preferably a carbonate buffer (for example, sodium hydrogencarbonate or sodium carbonate).

The sample, the active oxygen producing substance, and the buffer may be brought into contact with each other in any order, but it is preferable to bring the buffer into contact with the sample and then bring the active oxygen producing substance in contact therewith.

The buffer is generally used in a concentration of 10 to 500 mM, preferably 20 to 100 mM. The active oxygen producing substance is generally used in a concentration of 10 $\mu$M to 4 mM, but the optimum concentration varies depending on the type of the compound used. The phenazinium compound of the formula (1) is generally used in a concentration of 10 $\mu$M to 500 $\mu$M, preferably 40 $\mu$M to 200 $\mu$M. The bipyridine compound of the formula (2) is generally used in a concentration of 0.2 mM to 4 mM, preferably 0.5 mM to 2 mM. The 1,4-quinone compound of the formula (3) or the 1,2-quinone compound of the formula (4) is generally used in a concentration of 10 $\mu$M to 2 mM, preferably 25 $\mu$M to 1 mM. The tetrazolium salt of the formula (5) is generally used in a concentration of 0.1 mM to 2 mM, preferably 0.2 to 1 mM.

The contact among the sample, the active oxygen producing substance, and the buffer may be performed at the temperature usually used, that is, room temperature to about 40° C. (preferably about 25° to 37° C.). If the contact time is increased, the amount of the product increases along therewith, so there is no particular limitation on the contact time. In the case of application to an automatic analysis apparatus or from the viewpoint of precision of measurement, it is preferable that the contact be for at least about 5 minutes.

When reducible fructosamines are present in the sample, active oxygen is produced by the fructosamines and the active oxygen producing substance, then the active oxygen derives hydrogen peroxide When the tetrazolium salt of the formula (5) is used as the active oxygen producing substance, superoxide dismutase (generally 60 $\mu$g/ml to 4 mg/ml, preferably 125 $\mu$g/ml to 2 mg/ml) is employed so as to derive only hydrogen peroxide without producing a water insoluble formazane dye.

The derived hydrogen peroxide is measured by a known method. The "reagent producing a detectable change in the presence of the hydrogen peroxide" derived from the active oxygen comprises (i) a substance having a peroxidizing activity (hereinafter referred to as a peroxidizing activity substance: typically, peroxidase); and (ii) a dyestuff precursor which forms a color or changes color or a substance which emits fluorescence, in the presence of a peroxidizing activity substance.

More particularly, a detectable substance A is produced by the following reaction:

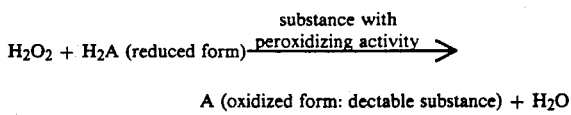

A (oxidized form: dectable substance) + H$_2$O wherein H$_2$A (reduced form) is a dyestuff precursor etc., and A (oxidized form: detectable substance) is a dyestuff etc. produced by the oxidation of H$_2$A.

The peroxidizing activity substance is, for example, peroxidase. Peroxidase exists in horseradish, potatoes, fig tree sap, turnip, milk (lactoperoxidase), leukocyte (myeloperoxidase), or microorganisms. Synthetic peroxidase may also be used.

As the peroxidizing activity substances other than enzymes, for example, there may be mentioned iron thiocyanate, iron tannate, iron (II) ferrocyanide, and dichromate (potassium chromium sulfate) absorbed in silica gel.

The dyestuff precursor which forms color or changes color in the presence of the peroxidizing activity substance is, for example, a monoamine (aniline or derivatives thereof, o-toluidine, p-toluidine, etc.), diamine (o-phenylene diamine, benzidine, dianisidine, etc.), phenol (phenol, thymol, cresol, naphthol, etc.), polyphenol (catechol, pyrogallolphloroglucinol, etc.), aromatic acids (salicylic acid, pyrocatechinic acid, gallic acid, etc.), leuco dyes (leuco-malechite green, leuco-phenol phthalein, etc.), and also dichlorophenol indole, epinephrine, and bilirubin.

According to a preferred embodiment of the present invention, the absorbance at the wavelength of 510 nm is measured within about 2 to 60 minutes after adding a suitable buffer solution (generally pH of 5 to 9) containing peroxidase (generally 2.5 to 50 $\mu$g/ml) and, as electron donors, 4-aminoantipyrine and 3-hydroxy-2,4,6-triiodobenzoic acid (generally 0.2 to 2 mM each) to the product of the step (a). As a control, distilled water is used.

Further, for the hydrogen peroxide produced, it is also possible to use the light emission method using luminol microperoxidase. Further, it is possible to use the fluorescent method using a fluorescent substance (for example, homovanillic acid).

The method of measurement of the present invention may be performed by a one step process wherein all the reagents are brought into contact with each other simultaneously (that is, adding the liquid sample into a system containing the active oxygen producing substance and the reagent producing a detectable change in the presence of hydrogen peroxide), but it is preferable to divide the procedures into two steps. That is, in the first step, the sample is brought into contact with the active oxygen producing substance to derive the hydrogen peroxide and then in the second step a detectable change is produced from the hydrogen peroxide and the degree of change is measured.

In the method of the present invention, it is possible to use any standard solution capable of determining the content by the HPLC method [Parker et al., Clinical Chemistry, 27, 669 to 671, 1981; Menez et al., J. Chromatography, 297, 339 to 350, 1984]. For example, it is possible to use the standard solution described in Japanese Examined Patent Publication No. 1-13062 (prepared from albumin and 1-deoxy-1-morpholinofructose)

or fructosyl glutamic acid (see specification of Japanese Patent Application No. 1-206721).

The principle of measurement of the present invention is based on the fact that in the presence of an oxidized substance, the electrons from a reducing enol form of fructosamines are used for a reaction to produce a peroxide dependent on the oxygen dissolved in solution. For example, in the presence of a suitable oxidized substance (the active oxygen producing substance of the present invention), electrons from the reducing enol form of fructosamines move to the oxygen dissolved in solution and active oxygen ($O_2^-$) is produced. Subsequently, the active oxygen produces hydrogen peroxide by a dismutation reaction:

$$2O_2^- + 2H^+ \rightarrow O_2 + H_2O_2$$

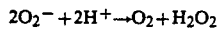

The dismutation reaction generally proceeds even without the presence of an enzyme etc., but when using a tetrazolium salt as the active oxygen producing substance, it is necessary to use superoxide dismutase so as to prevent a reaction from the tetrazolium salt to the formazane dye and on the other hand, so as to promote the above-mentioned dismutation reaction. The hydrogen peroxide derived by the dismutation reaction may be measured by methods known to persons skilled in the art.

EXAMPLES

The present invention now will be further illustrated by, but is by no means limited to, the following Examples.

EXAMPLE 1

Preparation of Standard Solutions

To Ringer's solution containing 0.4 mM glucose (Wako Junyaku), albumin extracted from serum and purified was added in an amount of 4.3 mg/ml. The whole was incubated at 37° C. for four days. The amount of the resulting glycosylated albumin was determined by the HPLC method [Parker et al., Clinical Chemistry, 27, 669 to 671, 1981; Menez et al., J. Chromatography, 297, 339 to 350, 1984] as a conversion to 5-hydroxymethyl-2-furfuraldehyde (5-HMF). A series of standard solutions having various concentrations from 10 μM to 200 μM was prepared. Further, distilled water was used as a control.

Preparation of Reagents

A carbonate buffer solution (20 mM; pH 10.0) containing 0.1 mM 9,10-phenanthrenequinone (9,10-PTQ) was prepared (referred to as a reagent A). A phosphate buffer solution (0.2M; pH 7.0) containing 2.8 mM 3-hydroxy-2,4,6-triiodobenzoic acid, 2.8 mM 4-aminoantipyrine, 0.55 mM ethylene diamine tetraacetic acid, and 11 μg/ml of peroxidase (derived from horseradish) was prepared (referred to as a reagent B).

Measurement Procedure

The standard solutions (50 μl each) were added to the reagent A (1.1 ml) and a reaction was performed at 37° C. for 5 minutes. To the reaction solution, 0.9 ml of the reagent B was added. The mixture was allowed to stand at room temperature for 10 minutes, and the absorbance at a wavelength of 510 nm was measured. A control experiment was also performed using distilled water instead of the standard solutions. The results are shown by the closed circle marks in FIG. 1.

EXAMPLE 2

Preparation of Reagents

A carbonate buffer solution (20 mM; pH 9.8) was prepared (referred to as a reagent A). An aqueous solution containing 10 mM 1-methoxy-5-methylphenazinium methylsulfate (1-methoxy PMS) was prepared (referred to as a reagent B). Further, a phosphate buffer solution (0.2M; pH 7.0) containing 2.8 mM 3-hydroxy-2,4,6-triiodobenzoic acid, 2.8 mM 4-aminoantipyrine, 0.55 mM ethylene diamine tetraacetic acid, and 11 μg/ml of peroxidase was prepared (referred to as a reagent C).

Measurement Procedure

The standard solutions (50 μl each) prepared in Example 1 were added to the reagent A (1.1 ml) and further 10 μl of the reagent B was added, and a reaction was performed at 37° C. for 5 minutes. To the reaction solution, 0.9 ml of the reagent C was added. The mixture was allowed to stand at room temperature for 10 minutes, and the absorbance at a wavelength of 510 nm was measured. A control experiment was also performed using distilled water instead of the standard solutions. The results are shown by the open circle marks in FIG. 1.

EXAMPLE 3

Preparation of Reagents

A carbonate buffer solution (10 mM; pH 10.3) containing 0.25 mM 3,3'-(3,3'-dimethoxy-4,4'-biphenylylene)-bis[2-(p-nitrophenyl)-5-phenyl-2H tetrazolium chloride] [Nitro-TB], 0.25 mM 4-aminoantipyrine, and 125 μg/ml of superoxide dismutase (SOD) was prepared (referred to as a reagent A). A phosphate buffer solution (0.1M; pH 6.0) containing 1.3 mM 3-hydroxy-2,4,6-triiodobenzoic acid, 1.8% Triton X-100, and 260 μg/ml of peroxidase was prepared (referred to as a reagent B).

Measurement Procedure

The standard solutions (50 μl each) prepared in Example 1 were added to the reagent A (1.1 ml) and a reaction was performed at 37° C. for 5 minutes. To the reaction solution, 0.25 ml of the reagent B was added. The mixture was allowed to stand at room temperature for 10 minutes, and the absorbance at a wavelength of 510 nm was measured. A control experiment was also performed using distilled water instead of the standard solutions. The results are shown by the X marks in FIG. 1.

EXAMPLE 4

Preparation of Reagents

A carbonate buffer solution (20 mM; pH 10.0) containing 0.3 mM 2-methyl-1,4-naphthoquinone was prepared (referred to as a reagent A). A phosphate buffer solution (0.2M; pH 7.0) containing 2.8 mM 3-hydroxy-2,4,6-triiodobenzoic acid, 2.8 mM 4-aminoantipyrine, 0.55 mM ethylene diamine tetraacetic acid, and 11 μg/ml of peroxidase (derived from horseradish) was prepared (referred to as a reagent B).

Measurement Procedure

The standard solutions (50 μl each) prepared in Example 1 were added to the reagent A (1.1 ml) and a reaction was performed at 37° C. for 5 minutes. To the reaction solution 0.9 ml of the reagent B was added. The mixture was allowed to stand at room temperature for 10 minutes, and the absorbance at a wavelength of 510 nm was measured. A control experiment was also performed using distilled water instead of the standard solutions. The results are shown by the triangle marks in FIG. 1.

EXAMPLE 5

Preparation of Reagents

A carbonate buffer solution (20 mM; pH 10.3) including 1 mM methyl viologen was prepared (referred to as a reagent A). A phosphate buffer solution (0.2M; pH 7.0) containing 2.8 mM 3-hydroxy-2,4,6-triiodobenzoic acid, 2.8 mM 4-aminoantipyrine, 0.55 mM ethylene diamine tetraacetic acid, and 11 μg/ml of peroxidase (derived from horseradish) was prepared (referred to as a reagent B).

Measurement Procedure

The standard solutions (50 μl each) prepared in Example 1 were added to the reagent A (1.1 ml) and a reaction was performed at 37° C. for 5 minutes. To the reaction solution 0.9 ml of the reagent B was added. The mixture was allowed to stand at room temperature for 10 minutes, and the absorbance at a wavelength of 510 nm was measured. A control experiment was also performed using distilled water instead of the standard solutions. The results are shown by the double circles in FIG. 1.

EXAMPLE 6

Serum was drawn from 24 persons and the content of fructosamines therein was measured by the method described in Example 1.

Figure 2:
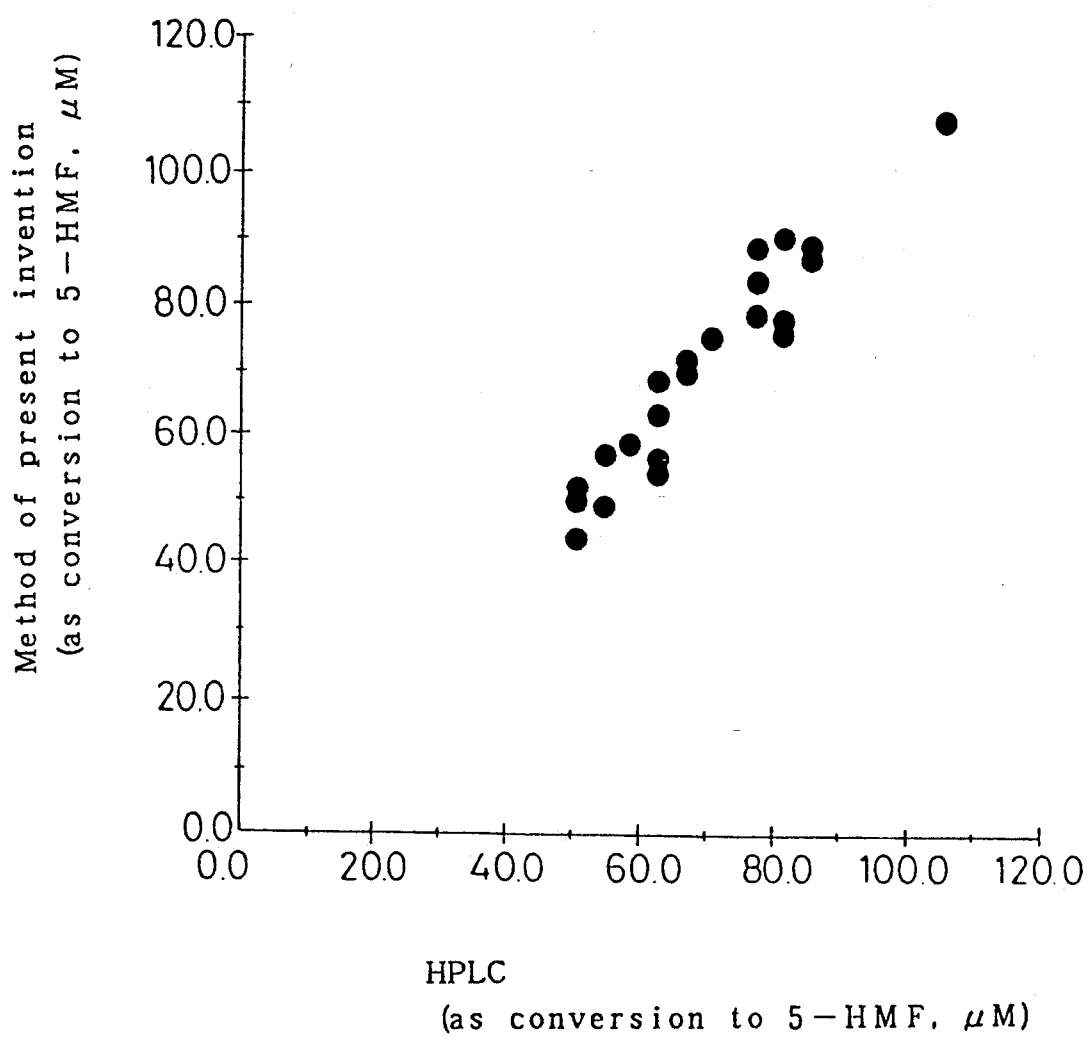
FIG. 2 is a graph showing the correlation between the method of the present invention and the conventional HPLC method.

Thereafter, the same serum samples were used for the measurement by the HPLC method [Parker et al., Clinical Chemistry, 27, 669 to 671, 1981; Menez et al., J. Chromatography, 297, 339 to 350, 1984] to investigate the correlation between the two methods. The results are shown in FIG. 2. As clear from FIG. 2, a good correlation was recognized and the coefficient of correlation was 0.946.

EXAMPLES 7 TO 10

The procedure described in Example 6 was repeated, but instead of 9,10-phenanthrenequinone, there were used 1-methoxy-5-methylphenazinium (Example 7), 2-methyl-1,4-naphthoquinone (Example 8), nitro-TB and superoxide dismutase (Example 9), and methylviologen (Example 10). The results are shown in the following Table 1.

TABLE 1

| Examples | Coefficient of correlation | Number of samples |
| --- | --- | --- |
| 7 | 0.918 | 24 |
| 8 | 0.924 | 24 |
| 9 | 0.909 | 24 |
| 10 | 0.894 | 24 |

Industry Applicability

According to the method of measurement of the present invention, no water insoluble color substance is formed, so it is possible to eliminate the problem of dispersion in the measurement values, colored substances adhering to the measurement equipment, etc. Further, interfering substances can be removed without affecting the measurement system, so it is possible to determine the measurement values at any time and further there is no need for measurement at two points. Therefore, it is possible to perform accurate measurement quickly and with a high precision.

We claim:

1. A method for measurement of fructosamines in an aqueous liquid which comprises the steps of:
   (a) bringing an aqueous liquid sample into contact with a 1,2-quinone compound of the general formula:

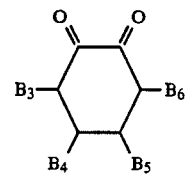

wherein, $B_3$ and $B_4$ are respectively hydrogen atoms or are atoms necessary for forming a benzene ring or a pyridine ring together with the two carbon atoms in the formula, and $B_5$ and $B_6$ are atoms necessary for forming a benzene ring or a pyrrole ring together with the two carbon atoms in the formula, said pyridine being substituted by carboxylic acid groups and said pyrrole ring being substituted by a carboxylic acid group, at a pH of from 8.5 to 11;
   (b) bringing the product of step (a) into contact with a reagent for measuring hydrogen peroxide for measuring hydrogen peroxide resulting from the reaction of step (a) between said 1,2-quinone compound and said fructosamines; and
   (c) measuring a detectable change in the reagent of step (b).

2. A process according to claim 1 wherein said 1,2-quinone compound is selected from the group consisting of 1,2-naphthoquinone, 9,10-phenanthrenequinone, and 2,7,9-tricarboxy-1H-pyrrolo[2,3-f]quinoline-4,5-dione.

3. A process according to claim 1, wherein the aqueous liquid sample is a biological aqueous liquid.

4. A process according to claim 1, wherein the reagent producing a detectable change in the presence of hydrogen peroxide comprises a substance having a peroxidizing activity and a dyestuff precursor which forms a color or changes color or a substance which emits fluorescence, in the presence of a peroxidizing activity substance.

5. A process according to claim 1, wherein the aqueous liquid sample is added to a system containing the active oxygen producing substance and the reagent producing a detectable change in the presence of hydrogen peroxide, and the occurrence of the detectable change is detected.

6. A process according to claim 1, wherein hydrogen peroxide is derived by bringing the sample into contact with the active oxygen producing substance; the detectable change is caused to occur by hydrogen peroxide; and the occurrence of the detectable change is detected.

* * * * *